United States Patent [19]
Xu et al.

[11] Patent Number: 5,602,647
[45] Date of Patent: Feb. 11, 1997

[54] APPARATUS AND METHOD FOR OPTICALLY MEASURING CONCENTRATIONS OF COMPONENTS

[75] Inventors: Kexin Xu; Yutaka Yamasaki; Harumi Uenoyama; Takeshi Sakura, all of Kyoto, Japan

[73] Assignee: Kyoto Daiichi Kagaku Co., Ltd., Kyoto-fu, Japan

[21] Appl. No.: 562,785

[22] Filed: Nov. 27, 1995

Related U.S. Application Data

[63] Continuation of Ser. No. 272,564, Jul. 11, 1994, abandoned.

[30] Foreign Application Priority Data

Jul. 14, 1993 [JP] Japan .................. 5-174156

[51] Int. Cl.$^6$ .................................................. G01N 21/00
[52] U.S. Cl. ..................... 356/435; 356/436; 356/440; 356/246
[58] Field of Search ................................. 356/435–436, 356/440, 246, 70; 250/576

[56] References Cited

U.S. PATENT DOCUMENTS

| | | | |
|---|---|---|---|
| 3,727,066 | 4/1973 | Louderback et al. | 356/436 |
| 3,746,864 | 7/1973 | Tick et al. | 250/576 |
| 4,786,171 | 11/1988 | Lefebre et al. | 356/436 |
| 4,893,935 | 1/1990 | Mandel et al. | 356/436 |
| 5,032,024 | 7/1991 | Cope | 356/435 |
| 5,268,736 | 12/1993 | Prather | 356/440 |
| 5,287,168 | 2/1994 | Poucher et al. | 356/436 |
| 5,303,036 | 4/1994 | McLachlan et al. | 356/440 |
| 5,309,213 | 5/1994 | Desjardins et al. | 356/436 |

FOREIGN PATENT DOCUMENTS

| | | | |
|---|---|---|---|
| 63-144237 | 6/1988 | Japan . | |
| 63-165736 | 7/1988 | Japan | 356/440 |
| 63-273043 | 11/1988 | Japan | 356/440 |
| 2193313 | 2/1988 | United Kingdom . | |

OTHER PUBLICATIONS

Schmidt et al "Absorption Cell With Variable Path Length" IBM Technical Disclosrue Bulletin, vol. 26, No. 9, Feb. 1994, pp. 4683–4684.

"A Variable–Pathlength Optical Cell with No Moving Parts" By R. J. Fiddik et al. *Journal of Physics E. Scientific Instruments*, vol. 21, 1988 pp. 1033–1037.

"Lens and Wedge Absorption Cells for FT–IR Spectroscopy" By T. Hirshfeld *Applied Spectroscopy*, vol. 39 No. 3, 1985, pp. 426–430.

*Primary Examiner*—Frank Gonzalez
*Assistant Examiner*—Jason D. Eisenberg

[57] ABSTRACT

An apparatus and method for optically measuring concentrations of components allow enhancement in measurement accuracy of concentration. The apparatus includes a cell, a light irradiator, a photodetector, and an arithmetic unit. The cell presents different optical path lengths at different locations and is to contain a sample therein. The light irradiator, which includes a variable-wavelength laser generator and a measuring system composed of convex lenses, outputs a collimated, enlarged laser beam, and makes the laser beam incident upon the cell. The photodetector comprises a multiplicity of photodetectors arranged in parallel to the surface of the cell, so that it can detect intensity of rays of transmitted light that have traveled over different optical path lengths at positions of an equal distance from the cell. The arithmetic unit, receiving a signal from the individual photodetectors, calculates concentrations of components in the sample based on optimum optical path lengths for different wavelengths and values of transmitted light at positions of the optimum optical path lengths, and further outputs calculation results.

16 Claims, 7 Drawing Sheets

APPARATUS AND METHOD FOR OPTICALLY MEASURING CONCENTRATIONS OF COMPONENTS

This application is continuation, of application Ser. No. 08/272,564 filed on Jul. 11, 1994, now abandoned.

BACKGROUND OF THE INVENTION

1. Field of the Invention

The present invention relates to an apparatus and a method for measuring concentrations of light-absorbing substances in an aqueous solution. More specifically, the invention relates to an apparatus and a method for optically measuring concentrations of components, which are applicable to measurement of, for example, concentrations of glucose and hemoglobin in blood, and concentrations of protein, bilirubin and saccharide in urine as well as concentrations of components in beverages.

2. Description of the Prior Art

It is well known that the relation between concentration of a solution and light absorption can be expressed by the following Lambert-Beer's law:

$$A_c = \mathrm{Log}_e(I_o/I_t) = \Sigma \alpha_i C_i L \tag{1}$$

where $A_c$ = absorbance, $I_o$ = quantity of incident light, $I_t$ = quantity of transmitted light, $\alpha_i$ = extinction coefficient of i component in the sample, $C_i$ = concentration of i component in the sample, and $L$ = optical path length within the cell containing the sample.

With regard to this equation, the concentration can be determined by performing multivariate analysis based on measured values of quantity of transmitted light on multiple wavelengths.

Since the concentrations of each component is determined based on measured values obtained by a measuring system, the accuracy of the concentration is limited by the measurement accuracy of the measuring system. Therefore, to determine the concentrations of components, particularly accurate concentrations of trace amounts of components out of the components to be measured, the measuring system is required to have an enhanced accuracy of measurement. Thus, the accuracy of the concentrations determined has a close relation to the S/N ratio of the measuring system.

Japanese Patent Laid-Open Publication No. 63-144237 (1988) has disclosed a method for measuring absorbances and an apparatus for the same, which are applicable to quantitative determination of trace amounts of organic and inorganic components in a sample solution.

This apparatus comprises a cell for a spectrophotometer having different cell lengths (i.e., optical path lengths, which herein mean distances over which light travels within a cell), a feeder for feeding a sample solution to the cell, a switching unit for switching over the optical path length, and a controller for controlling the feeder and the switching unit. According to this apparatus, measurement of absorbances of sample solutions is carried out based on the quantity of transmitted light at a portion of the cell corresponding to the short optical path length for high concentration samples or the quantity of transmitted light at another portion of the cell corresponding to the long optical path length for low concentration samples.

The above measuring method and apparatus incorporate a cell for a spectrophotometer, actually a triangular cell, having different optical path lengths, wherein the optical path length is switched over so that the absorbance falls within a range suited for measurement. Thus, the measuring method and apparatus are intended to accomplish a wide range of concentration measurement from low concentration sample solutions to high concentration sample solutions without necessitating dilution of the sample solution or exchange of the cell.

In the above measuring method and apparatus, the optical path length is switched to a path length such that the absorbance falls within a range suited for measurement depending on differences in concentration among sample solutions, without changing the wavelength of light applied to samples. However, for example, when one component contained in the samples is of almost the same concentration among the samples, like glucose in blood, the method and apparatus have a disadvantage that they could not enhance the measurement accuracy of the concentration of this component.

SUMMARY OF THE INVENTION

The present invention has been accomplished to solve the above problems of the prior art. An object of the invention is therefore to provide an apparatus and a method for optically measuring concentrations of components, which are capable of enhancing the measurement accuracy of concentrations, regardless of whether the differences in concentration of one component contained in samples are large or small.

To achieve the above object, according to a first aspect of the present invention, there is provided an apparatus for optically measuring concentrations of components, which comprises: a cell for containing a sample therein, the cell being capable of changing its internal optical path length; a light irradiator for irradiating light of a selected wavelength to the cell, the light irradiator being capable of changing the wavelength of to be irradiated; a photodetector for receiving light that has been transmitted through the cell to detect quantity of the transmitted light; and an arithmetic unit for calculating and storing for each wavelength an optical path length at which a peak value of quantity-of-light measuring sensitivity with respect to the quantity of transmitted light detected by the photodetector takes place, and calculating concentration of a component contained in the sample based on values of the quantity of transmitted light and values of the optical path length at peak positions, the values having been stored for each wavelength, and for outputting calculation results.

As a second aspect of the present invention, the cell has a continuously or stepwise different optical path lengths.

As a third aspect of the present invention, the cell has a variable optical path length.

As a fourth aspect of the present invention, the light irradiator has a laser generator capable of generating laser beams of different wavelengths.

As a fifth aspect of the present invention, the laser generator is a variable-wavelength laser generator.

As a sixth aspect of the present invention, the light irradiator comprises a variable-wavelength laser generator, and a measuring system for making laser beams from the variable-wavelength laser generator incident upon the cell in such a form that the laser beam has been enlarged in its beam cross-sectional area and formed into collimated light.

As a seventh aspect of the present invention, the light irradiator comprises a rotatable mirror for, upon reception of a laser beam, changing a direction in which the laser beam is reflected, and a measuring system for directing the reflected laser beam toward a specified direction.

As an eighth aspect of the present invention, the light irradiator comprises a light emitter for emitting light including different wavelengths, and a measuring system for allowing light only of a selected wavelength out of the light to become incident on the cell in the form of collimated light.

As a ninth aspect of the present invention, the apparatus for optically measuring concentrations of components further comprises a quantity-of-light detection means for detecting quantity of light when said photodetector has received selected light.

As a tenth aspect of the present invention, the photodetector comprises a spectrometer.

As an eleventh aspect of the present invention, there is provided a method for optically measuring concentrations of components, which comprises: a step for irradiating light of a wavelength selected by a light emitter capable of generating light of different wavelengths, to a cell which contains a sample therein and which is capable of changing optical path length over which light is transmitted; a step for detecting quantity of transmitted light for each optical path length when the photodetector has received light transmitted through the cell, the above steps being repeatedly performed for a plurality of wavelengths; and a step for calculating and storing for each wavelength an optical path length at which a peak value of quantity-of-light measuring sensitivity with respect to the quantity of transmitted light detected by the photodetector takes place, and calculating concentration of a component contained in the sample based on values of the quantity of transmitted light and values of the optical path length at peak positions, and for outputting calculation results, the step being performed by an arithmetic unit.

As a twelfth aspect of the present invention, the method comprises:

(i) a step for measuring quantity of transmitted light of a wavelength $\lambda$ that has been emitted from a light source and transmitted through a cell which does not contain a sample and calculating a quantity of incident light $I_o$ by the following equation:

$$I_t = I_o t \gamma$$

where
$I_o$ = quantity of light incident upon the cell,
$I_t$ = quantity of light transmitted through the cell,
$\gamma = \exp(-\Sigma \alpha_i C_i L - \alpha_c l)$
$l = l_1 + l_2$
$t: t_1 t_2 t_3 t_4 = t(n_o, n_c, n)$
$t_i$ = transmissivity at i interface,
$\alpha_i$ = extinction coefficient of i component (a function of wavelength),
$\alpha_c$ = extinction coefficient of the cell (a function of wavelength),
$C_i$ = concentration of i component in the sample,
$l_a$, $l_2$ = wall thicknesses on both sides of the cell, and
n, $n_o$, $n_c$ refractive indexes of sample, air, and cell, respectively, (ii) a step for calculating a transmissivity $t_s$ that depends on the refractive index of a reference concentration sample to the light of wavelength $\lambda$, (iii) a step for measuring a quantity of transmitted light $I_{to}$ of the light of wavelength $\lambda$ when an optical path length L within the cell is set to a reference optical path length $L_o$, in a state that the cell contains the reference concentration sample, (iv) a step for calculating a value $\gamma_o$ of $\gamma$ for light with the reference optical path length $L_o$ and the wavelength $\lambda$ by the following equation:

$$I_t = I_o t \gamma$$

(v) a step for calculating an optical path length ratio $k_p$ corresponding to an optical path length $L_p$ at which quantity-of-light measuring sensitivity S reaches a maximum with the wavelength $\lambda$, by the following equation:

$$k = -1/\log_e(\gamma_o \delta)$$

where
$\delta = \exp(\alpha_c l)$
the quantity-of-light measuring sensitivity S being defined by the following equation:

$$S = dI_t/d\ C_i$$

where
S = quantity-of-light measuring sensitivity,
$dI_t$ = variation of quantity of transmitted light $I_t$ based on variation $dC_i$ of i component concentration, and
$dC_i$ = variation of i component concentration, (vi) a step for calculating an optimum optical path length $L_{p\lambda}$ at which the quantity-of-light measuring sensitivity S reaches a maximum with the wavelength $\lambda$, by the following equation:

$$k = L/L_o$$

the above steps being performed repeatedly a plurality of times with the wavelength $\lambda$ varied, to calculate values of quantity of transmitted light at positions of optimum optical path lengths $L_{p\lambda}$ corresponding to the varied wavelengths $\lambda$, wherein concentration of a component contained in the sample is calculated by multivariate analysis based on the calculated values of quantity of transmitted light.

As a thirteenth aspect of the present invention, the method comprises:

(i) a step for measuring quantity of transmitted light of a wavelength $\lambda$ that has been emitted from a light source and transmitted through the cell which does not contain a sample and calculating a quantity of incident light $I_o$ by the following equation:

$$I_t = I_o t \gamma$$

where
$I_o$ = quantity of light incident upon the cell,
$I_t$ = quantity of light transmitted through the cell,
$\gamma = \exp(-\Sigma \alpha_i C_i L - \alpha_c l)$.
$l = l_1, l_2$
$t: t_1 t_2 t_3 t_4 = t(n_o, n_c, n)$
$t_i$ = transmissivity at i interface,
$\alpha_i$ = extinction coefficient of i component (a function of wavelength),
$\alpha_c$ = extinction coefficient of the cell (a function of wavelength),
$C_i$ = concentration of i component in the sample,
l, $l_2$ = wall thicknesses on both sides of the cell, and
n, $n_o$, $n_c$ = refractive indexes of sample, air, and cell, respectively, (ii) a step for calculating a transmissivity $t_s$ that depends on the refractive index of the light of wavelength $\lambda$ in a reference concentration sample, (iii) a step for measuring a quantity of transmitted light $I_{tL}$ of wavelength with an optical path length L within the cell containing the reference concentration sample, (iv) a step for calculating absorbances $A_{c\lambda}$ to the light of wavelength $\lambda$ at portions of the cell corresponding to different optical path lengths L, by the following equation:

$$\log_e(I_e/I_t) - \log_e(1/t) - \alpha_c l = A_c$$

where $$A_c = \Sigma \alpha_i C_i L$$

(v) a step for determining an absorbance $A_{c\lambda p}$ equal to $\log_e e$ from among the absorbances $A_{c\lambda}$ to the light of wavelength $\lambda$, and (vi) a step for storing an optical path length $L_p$ corresponding to the absorbance $A_{c\lambda p}$ to the light of wavelength $\lambda$, the above steps being performed repeatedly a plurality of times with the wavelength $\lambda$ varied, to calculate values of quantity of transmitted light at positions of optimum optical path lengths $L_{p\lambda}$ corresponding to the varied wavelengths $\lambda$, wherein concentration of a component contained in the sample is calculated by multivariate analysis based on the calculated values of quantity of transmitted light.

with the above-described arrangements, it becomes possible to determine concentrations of components in a sample from the quantity of transmitted light in such a state that the S/N ratio reaches a maximum for each wavelength.

DETAILED DESCRIPTION OF THE PREFERRED EMBODIMENTS

An embodiment of the present invention is now described with reference to the accompanying drawings.

Figure 1:
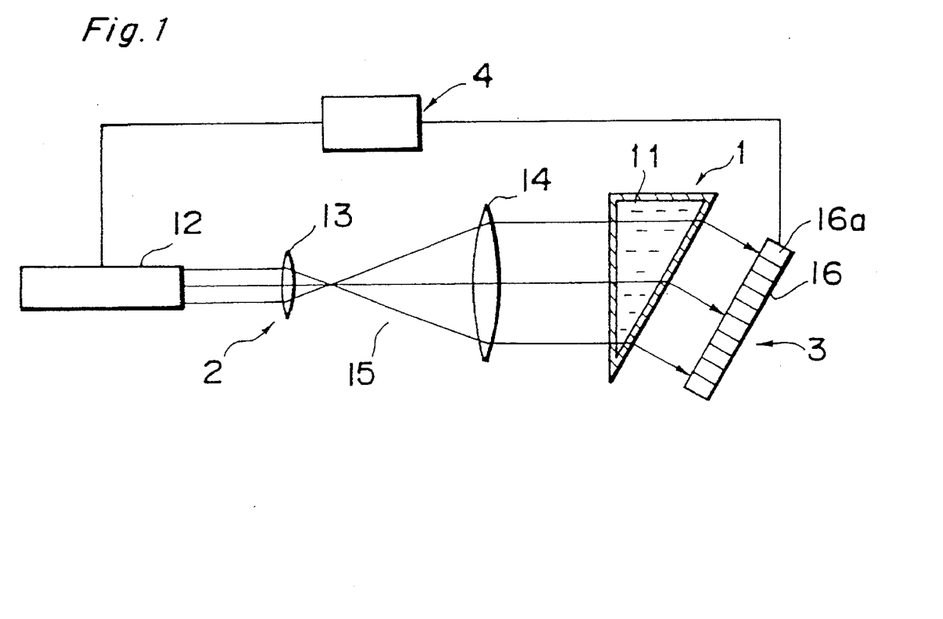
FIG. 1 is a diagram showing the outline of an apparatus for optically measuring concentrations of components according to the first, second, fourth, fifth, sixth and ninth aspects of the present invention, to which a method for optically measuring concentrations of components according to the eleventh, twelfth, and thirteenth aspects of the invention is applied.

FIG. 1 shows an apparatus for optically measuring concentrations of components according to the first, second, fourth, fifth, sixth, and ninth aspects of the present invention, to which a method for optically measuring concentrations of components according to the eleventh, twelfth, and thirteenth aspects of the invention is applied. This apparatus comprises a cell 1, a light irradiator 2, a photodetector 3, and an arithmetic unit 4.

The cell 1 is formed from a transparent member into a triangular shape in its cross section, and adapted to contain therein a sample 11 such as blood or urine. The cell 1 is arranged to be able to change its internal optical path length by changing the position in which the light is transmitted though the cell 1.

The light irradiator 2 comprises a variable-wavelength laser generator 12 capable of generating laser beams of different wavelengths, and a measuring system 15 composed of lenses 13, 14. A laser beam from the variable-wavelength laser generator 12 is focused on the focal point and then diverged by the lens 13 so that the laser beam is enlarged in cross-sectional area more than original, and further formed into collimated light by the lens 14. Then, the laser is incident upon the cell 1. It is noted that for the present invention the measuring system 15 is not limited to the combination of the lenses 13, 14 as far as the laser beam can be enlarged in cross-sectional area and formed into collimated light.

The photodetector 3 is provided by a quantity-of-light detection means 16, e.g. a CCD, composed of a multiplicity of quantity-of-light detection elements 16a, e.g. pixels, arranged in parallel to the surface of the cell 1 through which light goes out. Thus, it is possible to detect quantities of transmitted light that have traveled over different optical path lengths within the cell 1 at positions of an equal distance from the cell The arithmetic unit 4 receives a signal of quantity of transmitted light from the quantity-of-light detection elements 16a while it is connected to the variable-wavelength laser generator 12. Thus, the arithmetic unit 4 is capable of obtaining correspondence among the signal of quantity of transmitted light, optical path length and wavelength of transmitted light. In this arrangement, the arithmetic unit 4 derives an optimum optical path, at which the quantity-of-transmitted-light measuring sensitivity shows peak value, based on the above-described Lambert-Beer's formula (1) and Fresnel's formula, and calculates concentrations of components in the sample 11, such as those of glucose, hemoglobin, protein, bilirubin, and saccharide, based on the value of quantity of transmitted light at the position resulting the peak value. Then, the arithmetic unit 4 outputs calculation results.

Figure 2:
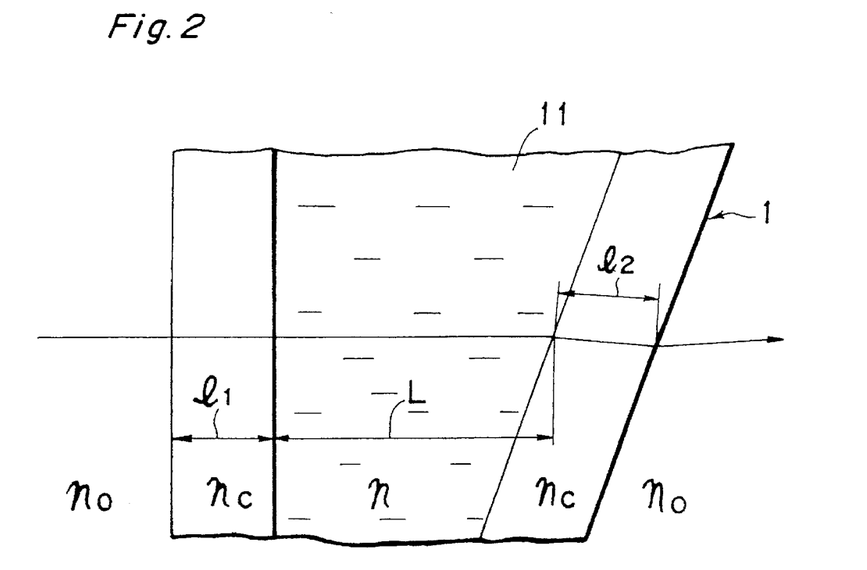
FIG. 2 is an enlarged sectional view of the cell the apparatus shown in FIG. 1.

More specifically, the calculation of component concentrations is accomplished by the following equations:

The quantity of transmitted light $I_t$ can be expressed by the following equation:

$$I_t = I_o t \gamma \quad (2)$$

where $\gamma = \exp(-\Sigma \alpha_i C_i L - \alpha_c l)$ $l = l_1 + l_2$ $t : t_1 t_2 t_3 t_4 = t(n_o, n_c, n)$ $t_i$ = transmissivity at i interface, $\alpha_i$ = extinction coefficient of i component (a function of wavelength), $\alpha^c$ = extinction coefficient of the cell 1 (a function of wavelength), $C_i$ = concentration of i component in the sample 11, $l_1$, $l_2$ = wall thicknesses on both sides of the cell 1, as shown in FIG. 2, and $n$, $n_o$, $n_c$ = refractive indexes of sample, air, and cell 1, as shown in FIG. 2, respectively.

Note that the $l$, $\alpha_c$, $n_o$, and $n_c$ are previously calculated. Also the t, $\alpha_i$, and n are previously calculated by the measurement using a plurality of liquid samples whose concentrations are known.

$$I_o/I_t = (1/t)\exp(\Sigma a_i C_i L + \alpha_c l) \quad (3)$$

$$\log_e(I_o/I_t) = \log_e(1/t) + \Sigma \alpha_i C_i L + \alpha_c l$$
$$= A_n + A_c$$
$$= A$$

where $A_n = \log_e(1/t) + \alpha_c l$ $A_c = \Sigma \alpha_i C_i L \quad (4)$ $A$: assumed absorbance where $A_n$ is a function of the refractive indexes of the cell and aqueous solution, the extinct/on coefficient of the cell, and the wall thicknesses of the cell, while $A_c$ is a function of the extinction coefficient of the solution, concentrations of components in the solution, and the optical path length L as shown in FIG. 2. They are commonly called absorbances.

For example, in the case of a glucose aqueous solution, where $\Sigma C_i = 1$, then $$\begin{aligned} I_t &= I_o t \exp(-\alpha_g C_g L - \alpha_w C_w L - \alpha_c L) \\ &= I_o t \exp\{-(\alpha_g - \alpha_w)C_g L - \alpha_w L - \alpha_c l\} \end{aligned}$$

Further, the quantity-of-light measuring sensitivity S for the i component in the sample 11 is defined as follows:

$$S = dI_t/dC_i \quad (5)$$

where $dI_t$ = variation of quantity of transmitted light $I_t$ based on variation of i component concentration $dC_i$, $dC_i$ = variation of i component concentration.

From Eq. (5), $$\begin{aligned} S &= I_o\{\gamma(dt/dn)(dn/dC_i) + t(d\gamma/dC_i)\} \\ &= I_o \gamma t F(n_c, n, \eta) + I_o \gamma t L(\alpha_w - a_i) \end{aligned} \quad (6)$$

where $\eta = dn/dC_i$

In this case, $dC_i$ is equal to $-dC_w$ since $C_i + C_w = 1$.

Substituting $S_n$ for the first term of the right side of Eq. (6) and $S_c$ for the second term yields $$S = S_n + S_c \quad (7)$$

With respect to the quantity-of-light measuring sensitivity S, $S_n$ of the right side of Eq. (7) represents a term that depends on the refractive index and $S_c$ represents a term that depends on the light absorption of each component.

In the equation (3) representing the assumed absorbances A, $A_n$ denotes an apparent absorbance based on the refractive index of a measurement object and the material of the cell, and $A_c$ depends linearly on the concentration of the sample that is the measurement object. Similarly, also in the quantity-of-light measuring sensitivity S, $S_n$ is an apparent quantity-of-light measuring sensitivity. Therefore, $S_n$ can be treated as a term for correction in the processing by electric circuits or in data arithmetic operations, like $A_n$.

Hence, the quantity-of-light measuring sensitivity that depends directly on the concentration of the measurement object is defined as $$S_c = S - S_n \quad (8)$$

With the quantity-of-light measuring sensitivity at a wavelength $\lambda$ assumed as $S_{c\lambda}$, Eq. (8) is reduced to $$S_{c\lambda} = S_\lambda - S_{n\lambda} \quad (9)$$

Then $$S_{c\lambda}/S_{n\lambda} = f(L, n, \alpha_w - \alpha_i, \eta) \quad (10)$$

Thus, from Eqs. (6) and (9)

$$S_{c\lambda} = I_0\gamma t L(\alpha_w - \alpha_i) \quad (11)$$
$$= g(\lambda, \gamma, L)$$

Since $$dS_{c\lambda}/dL=0 \quad (12)$$

the following equation results:

$$1-\Sigma\alpha_{i\lambda}C_jL=0$$

Hence, the following expression can be obtained:

$$L=1/\Sigma\alpha_{i\lambda}C_j \text{(Let L be } L_{p\lambda})$$

At this point, the quantity-of-light measuring sensitivity $S_{c\lambda}$ reaches a maximum, the maximum value being expressed as $S_{c\lambda max}$.

Also, the absorbance $A_p(=\log_e(I_0/I_{p\lambda}))$ at this point is $$-A_p=\Sigma\alpha_i C_i=1$$

As shown above, with respect to light of one wavelength $\lambda$, there exists an optimum optical path length $L_{p\lambda}$ that brings the quantity-of-light measuring sensitivity $S_{c\lambda}$ to a maximum value $S_{c\lambda max}$.

More specifically, the optical path length $L_{p\lambda}$ can be calculated from a ratio of quantity-of-light measuring sensitivities $S_{c\lambda}$ at different optical path lengths, as shown below.

From the equation $$S_{c\lambda L}=I_0 t(\alpha_w-\alpha_i)\gamma L \quad (14)$$

the absorption-dependent term $S_{c\lambda Lo}$ of the quantity-of-light measuring sensitivity at the reference optical path length $L_o$ can be expressed by the following equation:

$$S_{c\lambda Lo}=I_0 t(\alpha_w-\alpha_i)\gamma_o L_l \quad (15)$$

If the ratio of $S_{c\lambda L}$ to $S_{c\lambda Lo}$ is set to M, then $$M = S_{c\lambda L}/S_{c\lambda Lo} \quad (16)$$
$$= \gamma L/\gamma_o L_o$$
$$= k\gamma_o^{(k-1)}\delta^{(k-1)}$$

where $$k=L/L_o \quad (17)$$

$$\delta=\exp(\alpha_c l)$$

where $\delta$ is determined by the previously determined $\alpha_c$ and $l$.

dM/dk=0

Further, from Eq. (17), if $$k(=L/L_o)=-1/\log_e(\gamma_o\delta)(\text{Let } k \text{ be } k_p) \quad (18)$$

then M reaches a maximum so that $S_{c\lambda}$ reaches a maximum. The resulting value of M at this point is represented as $M_{max}$.

In other words, an optimum optical path length $L_{p\lambda}$ that brings the quantity-of-light measuring sensitivity $S_{c\lambda}$ to a maximum is calculated. Also, this optimum optical path length $L_{p\lambda}$ is calculated for each wavelength.

It is noted that $\gamma_o$ and $\delta$ are a measurable quantity and a constant, respectively.

Then, the absorbance $A_{c\lambda}$ is calculated based on the optimum optical path length $L_{p\lambda}$ for each necessary wavelength and the value of quantity of transmitted light corresponding thereto, and the i component concentration in the sample is calculated by multivariate analysis.

Figure 3:
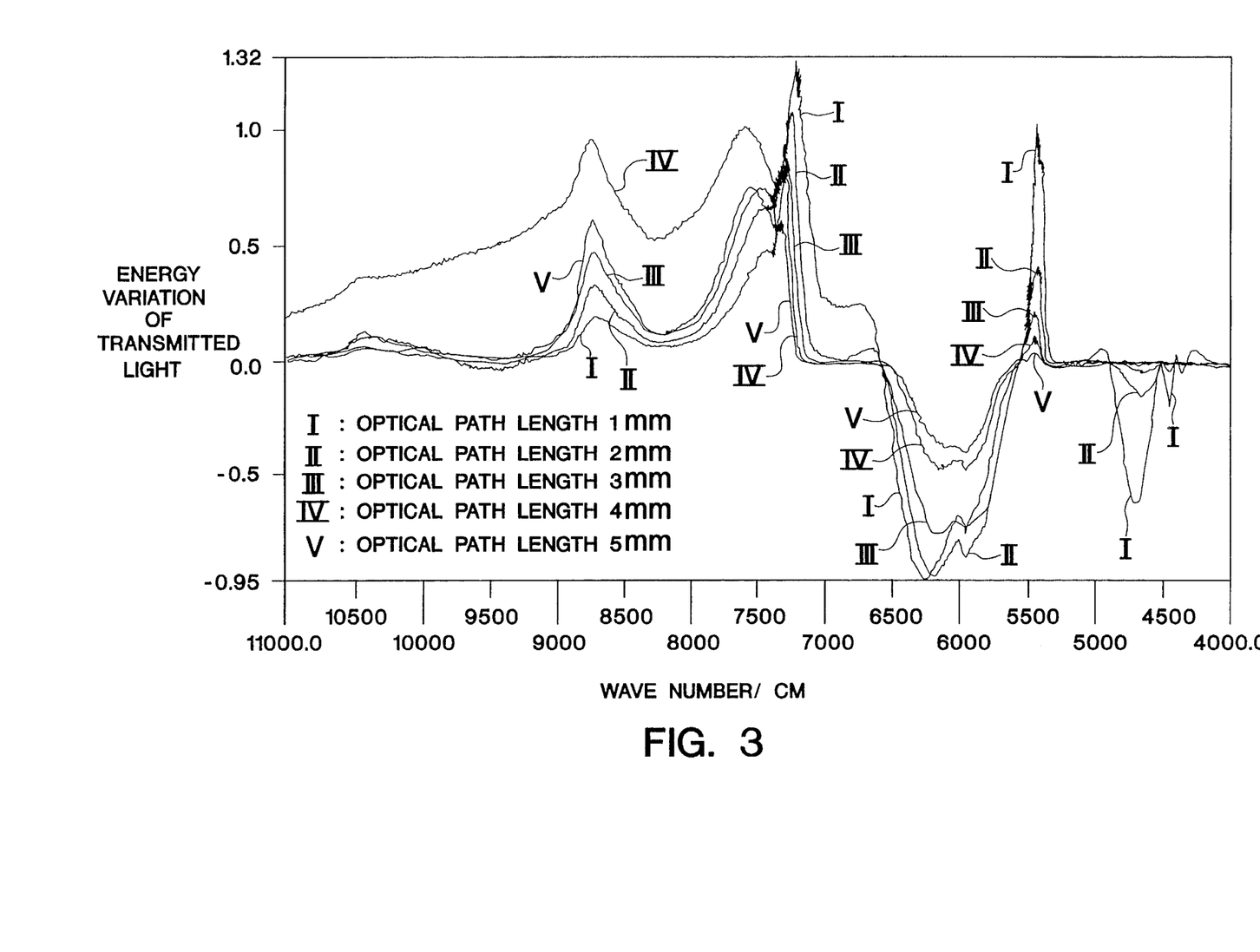
FIG. 3 is a chart showing measurement results of the relation between variation of quantity of transmitted light and wave number in a glucose solution, measured by an apparatus as shown in FIG. 13.
Figure 4:
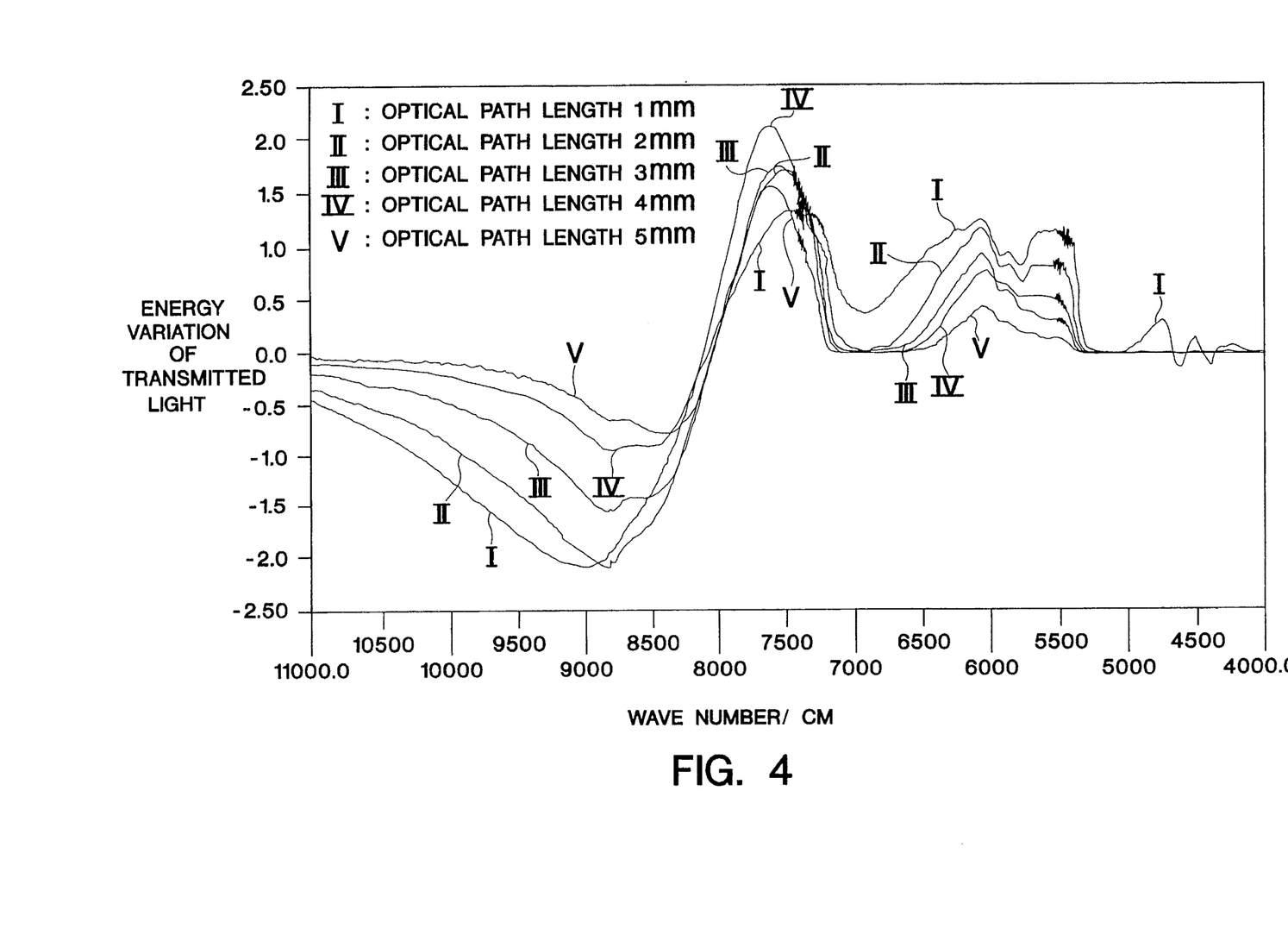
FIG. 4 is a chart showing measurement results of the relation between variation of quantity of transmitted light and wave number in solutions containing hemoglobin at two kinds of concentrations, measured by the apparatus as shown in FIG. 13.
Figure 13:
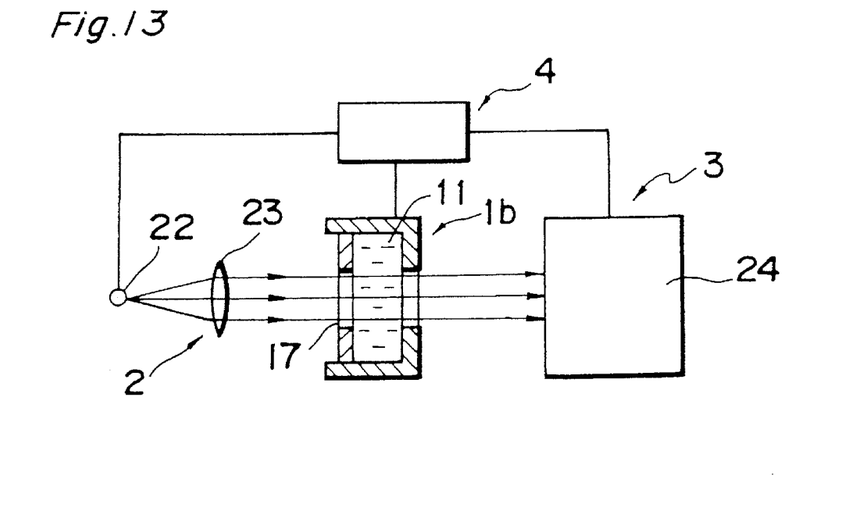
FIG. 13 is a diagram showing the outline of an apparatus for optically measuring concentrations of components according to the first, third, eighth, and tenth aspects of the present invention, to which the method for optically measuring concentrations of components according to the eleventh, twelfth, and thirteenth aspects of the present invention is applied.

FIGS. 3 and 4 show results of measurement of variations of transmitted light ($dI_t$) relative to unit variation of concentration (dC=1), with the use of an apparatus as shown in FIG. 13 described later, on aqueous solutions containing glucose of two kinds of concentrations in FIG. 3 and on aqueous solutions containing hemoglobin of two kinds of concentrations in FIG. 4. Both of FIGS. 3 and 4 show the fact that different wave numbers (wavelengths) result in different relations between variation of quantity of transmitted light and optical path length, as well as the fact that for each wavelength there exists an optical path length at which the variation of quantity of transmitted light reaches a maximum.

Figure 5:
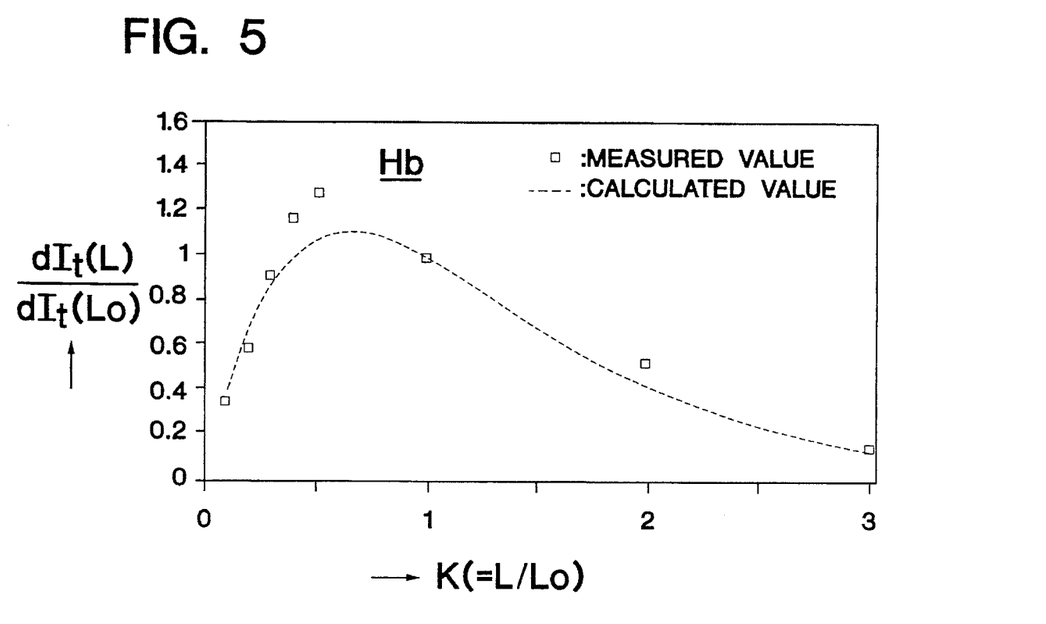
FIG. 5 is a chart showing the relation between optical path length ratio and variation ratio of quantity of transmitted light in a solution containing hemoglobin.
Figure 6:
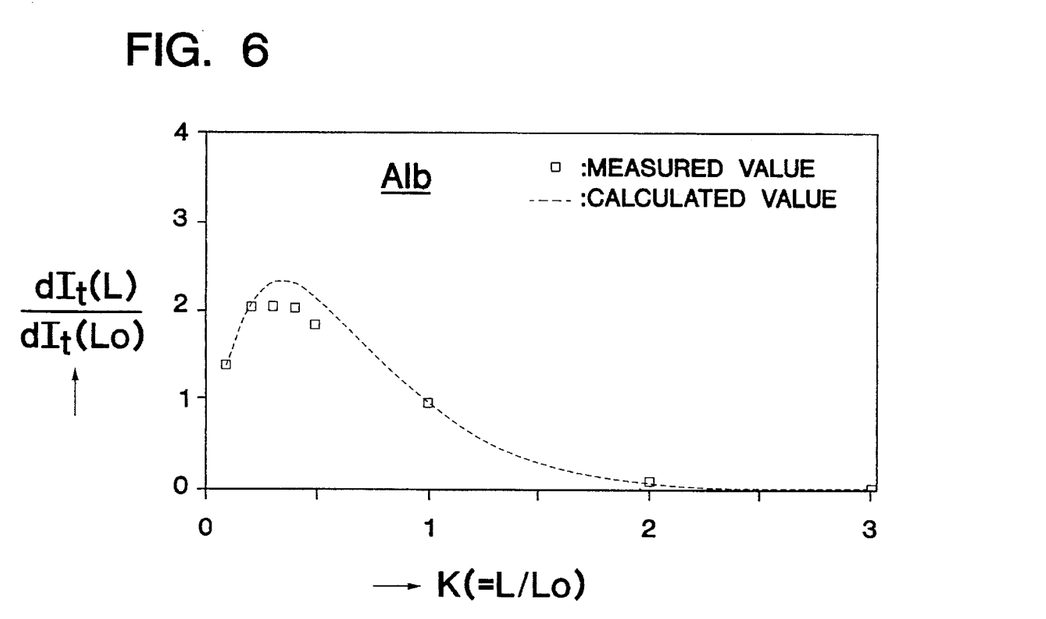
FIG. 6 is a chart showing the relation between optical path length ratio and variation ratio of quantity of transmitted light in a solution containing albumin.
Figure 7:
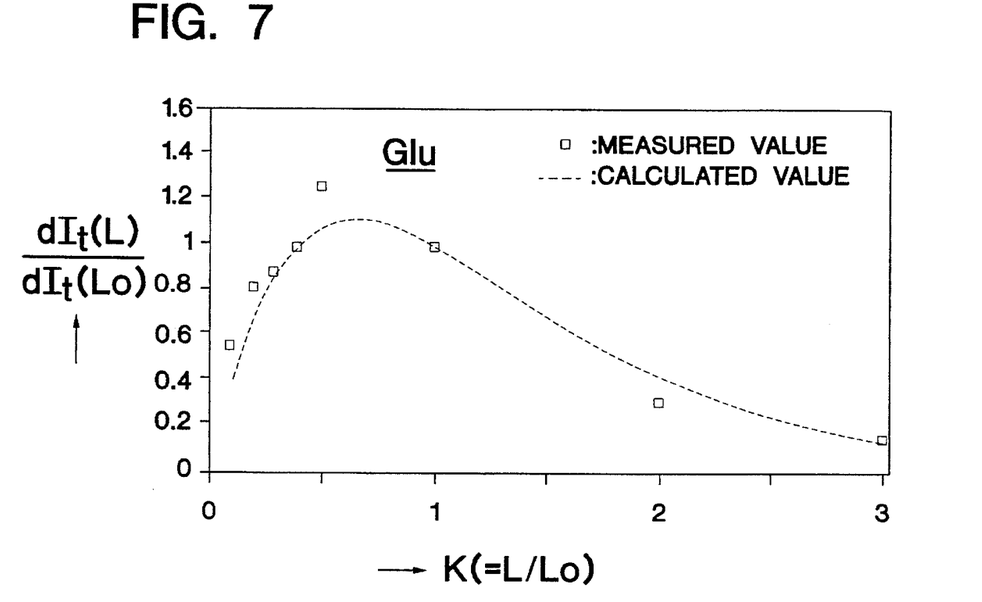
FIG. 7 is a chart showing the relation between optical path length ratio and variation ratio of quantity of transmitted light in a solution containing glucose.
Figure 9:
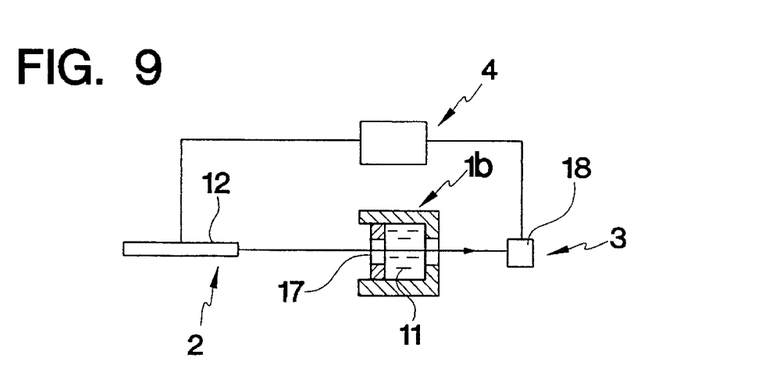
FIG. 9 is a diagram showing the outline of an apparatus for optically measuring concentrations of components according to the first, third, fourth, fifth, and ninth aspects of the present invention, to which the method for optically measuring concentrations of components according to the eleventh, twelfth, and thirteenth aspects of the present invention is applied.

Further, FIGS. 5, 6, and 7 show results of measurement of the relation between the ratio k ($=L/L_o$) of the optical path length L relative to the reference optical path length ($L_o$) and the variation ratio of quantity of transmitted light ($dI_t(L)$) through light path length L relative to quantity of transmitted light ($dI_t(L_o)$) through light path length $L_o$, with the use of an apparatus as shown in FIG. 9 described later, and light of a single wavelength, as well as results of arithmetic operations on the aforementioned relation, on an aqueous solution containing hemoglobin in FIG. 5, on an aqueous solution containing albumin in FIG. 6, and on an aqueous solution containing glucose in FIG. 7. These figures also show that there exists an optimum optical path length in each case.

As described above, in this apparatus, the concentration of the i component in the sample 11 is calculated and outputted by the arithmetic unit 4 from measurement data of large S/N ratios at optimum optical path lengths $L_{p\lambda}$ where the quantity-of-light measuring sensitivity reaches a maximum. Accordingly, the apparatus is capable of measuring the concentration of a component in a sample with high accuracy. In particular, the apparatus is suitable for measurement of the concentration of a component when the concentrations of the component have small differences among different samples.

Figure 8:
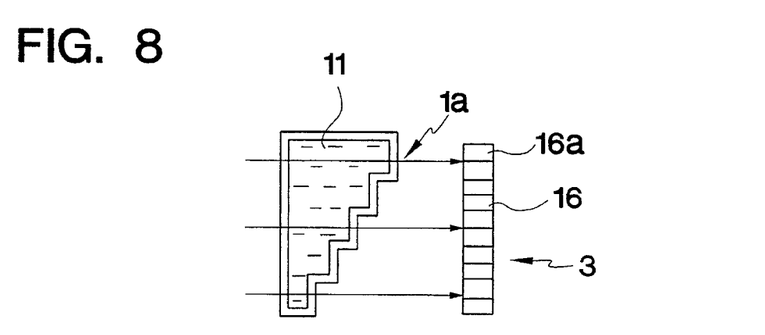
FIG. 8 is a diagram showing a modification example of the cell in the apparatus shown in FIG. 1.

The present invention is not limited to the above embodiment. For example, instead of the cell 1 of the triangular shape in cross section, a cell 1a whose optical path length will vary stepwise may be used as shown in FIG. 8.

Furthermore, it may also be arranged that the light irradiator 2 is provided only by the variable-wavelength laser generator 12, in which case the variable-wavelength laser generator 12, the cell 1, and the photodetector 3 are made relatively movable in a direction perpendicular to the optical axis so that the laser beam is incident upon portions of the cell of different optical path lengths one after another.

FIG. 9 shows an apparatus for optically measuring concentrations of components according to the first, third, fourth, fifth, and ninth aspects of the present invention, to which the method for optically measuring concentrations of components according to the eleventh, twelfth, and thirteenth aspects of the invention is applied. In the figure, parts common to FIG. 1 are designated by like numerals and omitted in their description.

A cell 1b of the present embodiment has a rectangular shape in cross section, and one optical transmitting portion 17 out of two optical transmitting portions of the cell 1b perpendicular to the laser beam derived from the light irradiator 2 is arranged to be movable right and left in FIG. 9. That is, the cell 1b has a movable optical path length. The photodetector 3 is provided by a quantity-of-light detection means 18 for detecting quantities of transmitted light of different wavelengths at a single and therefore equal position.

With the above arrangement, measurement of component concentrations is carried out by changing variously the position of the optical transmitting portion 17, so that quantities of transmitted light at different optical path lengths and different wavelengths are measured as in the case of the foregoing embodiment. Thus, based on the values of optimum optical path lengths and the values of quantity of transmitted light at peak positions of the quantity-of-light measuring sensitivity for different wavelengths, concentrations of components in the sample are calculated.

Figure 10:
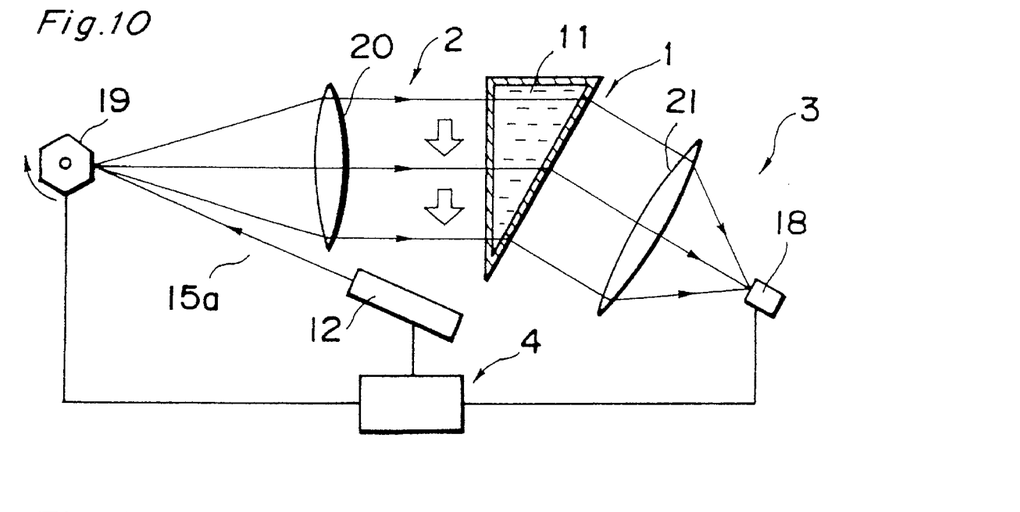
FIG. 10 is a diagram showing the outline of an apparatus for optically measuring concentrations of components according to the first, second, fourth, fifth, seventh, and ninth aspects of the present invention, to which the method for optically measuring concentrations of components according to the eleventh, twelfth, and thirteenth aspects of the present invention is applied.

FIG. 10 shows an apparatus for optically measuring concentrations of components according to the first, second, fourth, fifth, seventh, and ninth aspects of the present invention, to which the method for optically measuring concentrations of components according to the eleventh, twelfth, and thirteenth aspects of the invention is applied. In the figure, parts common to the aforementioned apparatus are designated by like numerals and omitted in their description.

In the present embodiment, the light irradiator 2 comprises a variable-wavelength laser generator 12, and a measuring system 15a including a rotatable mirror 19 and lenses 20, 21. Also, it is arranged that the position at which the laser beam derived from the variable-wavelength laser generator 12 is incident upon the rotatable mirror 19 coincides with the focal point of the lens 20. Then, the laser beam is reflected by the rotatable mirror 19 in various directions, where laser beams which are incident upon the lens 20 at different positions travel parallel to the optical axis of the lens 20 and then are incident upon the surface of the cell 1 perpendicularly thereto at different positions of the cell 1.

The photodetector 3 comprises a lens 21 and a single quantity-of-light detection means 18 arranged at the position of the focal point of the lens 21. The arithmetic unit 4, the variable-wavelength laser generator 12, the quantity-of-light detection means 18, and the rotatable mirror 19 are connected to one another, so that correspondence can be achievable between quantity of detected light and laser wavelength, mirror rotation angle, and optical path length. Then, the laser beams that have been transmitted through portions of different optical path lengths of the cell 1 are conducted to the quantity-of-light detection means 18 by the lens 21, where the quantity of light is measured on the transmitted light of the laser beams that have passed through the different optical path lengths. Also, similar measurement is repeated by changing wavelengths of the laser derived from the variable-wavelength laser generator 12. Then, as in the case of the foregoing embodiment, concentrations of components are calculated based on optimum optical path lengths for different wavelengths and values of transmitted light at peak positions of the quantity-of-light measuring sensitivity, and calculation results are outputted.

Figure 11:
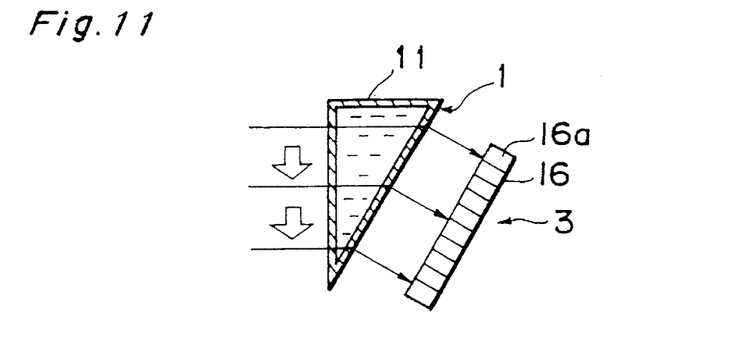
FIG. 11 is a diagram showing a cell and a photodetector used instead of the cell and the photodetector shown in FIG. 10.

It is noted that, in the above embodiment, the photodetector 3 may also be provided by a quantity-of-light detection means 16 composed of a multiplicity of quantity-of-light detection elements 16a arranged in parallel to the surface of the cell 1, as shown in FIG. 11. In this case, it is possible to detect each of the quantity of transmitted light that have traveled over different optical path lengths, at positions of an equal distance from the cell 1.

Figure 12:
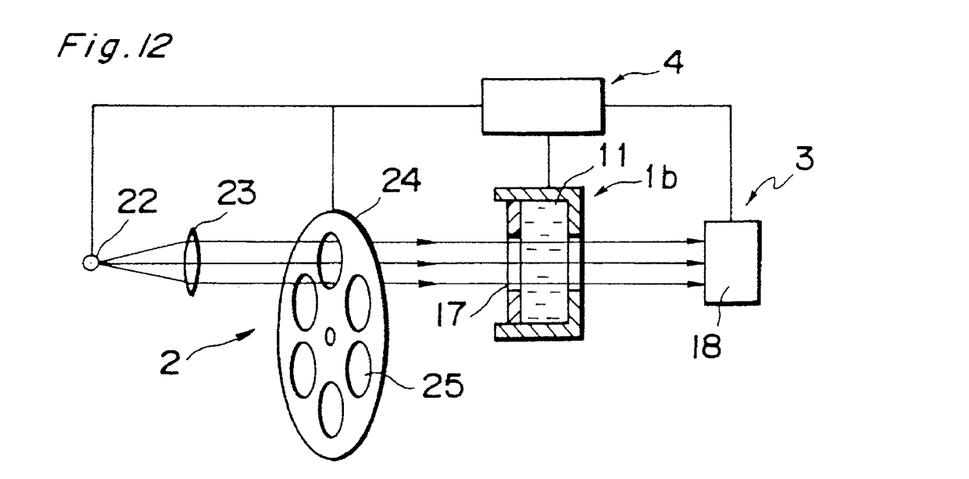
FIG. 12 is a diagram showing the outline of an apparatus for optically measuring concentrations of components according to the first, third, eighth, and ninth aspects of the present invention, to which the method for optically measuring concentrations of components according to the eleventh, twelfth, and thirteenth aspects of the present invention is applied.

FIG. 12 shows an apparatus for optically measuring concentrations of components according to the first, third, eighth, and ninth aspects of the present invention, to which the method for optically measuring concentrations of components according to the eleventh, twelfth, and thirteenth aspects of the invention is applied. In the figure, parts common to the apparatuses shown in FIGS. 1, 2, and 8 through 11 are designated by like numerals and omitted in their description.

In the present embodiment, the light irradiator 2 comprises a lamp 22 for irradiating light including different wavelengths, a convex lens 23, and a rotatable spectral disc 24. The spectral disc 24 has a plurality of different filters 25, which transmit only light of their corresponding wavelengths.

Then, light derived from the lamp 22 is formed into collimated light by the lens 23, where only light of a selected wavelength is incident upon the cell 1b, which is in a state of one optical path length, via any corresponding one of the filters 25. The light that has been transmitted through the cell 1b is incident upon the photodetector 3 provided by the single quantity-of-light detection means 18, where the resulting quantity of transmitted light is measured.

Subsequently, similar measurement is performed by changing the optical path length of the cell 1b. Further, with the filter 25 changed by rotating the spectral disc 24 through a predetermined angular pitch, similar measurement is repeated by using light of a different wavelength. Thus, as in the case of the foregoing embodiments, concentrations of components are calculated based on the optimum optical path length for each wavelength and the values of quantity of transmitted light at peak positions of the quantity-of-light measuring sensitivity.

It is noted that the arithmetic unit 4, the spectral disc 24, and the cell 1b are connected to one another, where correspondence can be performed among quantity of detected light and one of the filters 25 transmitting the light and optical path length.

FIG. 13 shows an apparatus for optically measuring concentrations of components according to the first, third, eighth, and tenth aspects of the present invention, to which the method for optically measuring concentrations of components according to the eleventh, twelfth, and thirteenth aspects of the invention is applied. In the figure, parts common to the apparatuses shown in FIGS. 1, 2, and 8 through 12 are designated by like numerals and omitted in their description.

In the present embodiment, the light irradiator 2 comprises a lamp 22 and a lens 23. The photodetector 3 is equipped with a spectrometer 24.

Then, light derived from the lamp 22 including different wavelengths is formed into collimated light by the lens 23 and is incident upon the cell 1b, which is in a state of one optical path length. The light that has been transmitted through the cell 1b is separated into its spectral components by the spectrometer 29, so that quantity of transmitted light is measured for each wavelength. Thereafter, similar measurement is repeated by changing optical path lengths of the cell 1b, where concentrations of components are calculated in the same way as in the foregoing embodiments.

It is noted that the arithmetic unit 4 and the cell 1b are connected to each other, so that correspondence can be performed between quantity of detected light and optical path length.

In the embodiments as shown in FIGS. 12 and 13, the measuring system that makes collimated light incident upon the spectral disc 24 or the cell 1b has been formed of only the lens 23. However, this is not limitative.

Figure 14:
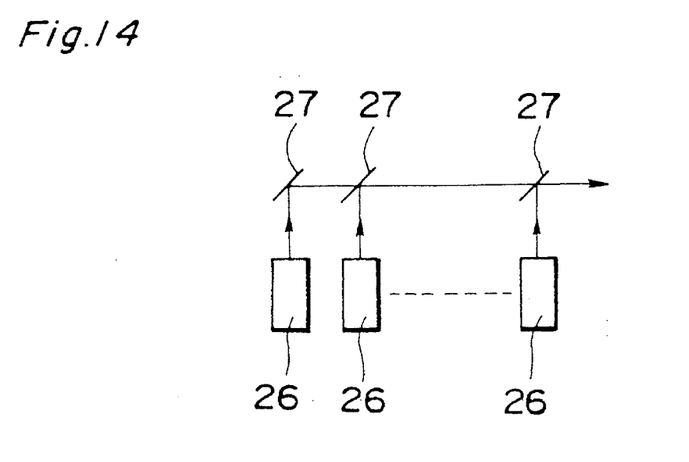
FIG. 14 is a diagram showing a light-irradiating means used instead of the lamp shown in FIG. 13 or the laser of FIGS. 1, 9, and 10.

FIG. 14 shows a modified example of the light-irradiating means for generating light including different wavelengths, wherein there are also provided a plurality of laser beams diodes (LDs) 26 for generating laser beams of different wavelengths, and semi-transparent mirrors 27 in correspondence to each of the LDs 26. These mirrors 27 are moved so as to reflect only laser of particular wavelengths derived from their corresponding LDs 26, and not to reflect light of other wavelengths. Further, reflected light from the mirrors 27 is made to travel along the same optical axis, so that light having a plurality of wavelengths are irradiated.

Figure 15:
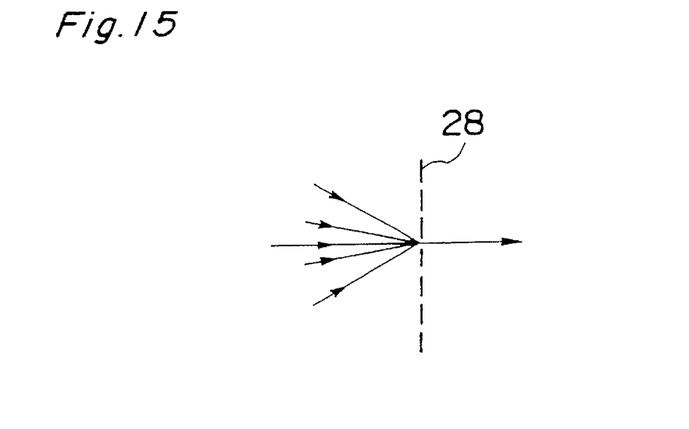
FIG. 15 is a diagram showing another light-irradiating means used instead of the lamp in the apparatus shown in FIG. 13.

FIG. 15 shows another modified example of the light-irradiating means for generating light including different wavelengths, wherein light including different wavelengths is irradiated by using a diffraction grating 28.

Instead of the lamp 22 as shown in FIG. 12 and FIG. 13, the light-irradiating means as shown in FIG. 14 and FIG. 15 may be used.

Next described is the method for optically measuring concentrations of components according to the eleventh aspect of the present invention which is applied, for example, to the apparatus as shown in FIG. 1.

First, in a state that the cell 1 does not contain the sample 11, laser of a wavelength $\lambda_j$ (j=1) is emitted from the variable-wavelength laser generator 12.

The laser is formed into collimated light via the measuring system 15 and is incident upon different positions of the cell 1, thus light that has passed over different optical path lengths in the air is incident upon different quantity-of-light detection elements 16a. Then, by an electrical signal from the $N_i$th quantity-of-light detection element 16a (the $N_i$th quantity-of-light detection element 16a corresponds to a transmission position of light that has passed a portion of the cell of an optical path length $L_{ij}$), the quantity of transmitted light $I_{aij}$ that has passed over the optical path length $L_{ij}$ is measured.

Then, based on the measured Iaij and $\delta 1 = \exp(\alpha_c - 1))$ which is previously determined, and using Eq. (2), the quantity of incident light $I_o$ of light transmitted through the reference optical path length is calculated.

Similar measurement is performed for laser beams of various wavelengths $\lambda_j$ (j=2 to m) and the quantities of respective incident light are calculated.

Subsequently, in a state that the cell 1 contains the sample 11, the quantity of light $I_{tij}$ that has been transmitted through the portions of the various wavelengths $L_{ij}$ of the sample 11 of the reference concentration within the cell 1 is measured in the same way as in the above case.

Based on the measured $I_{aij}$, $I_{tij}$ (j=1 to m), $k_p$ is calculated from Eq. (2) and Eq. (18), while optimum optical path lengths $L_{pj}$ (j=1 to m) at which the quantity-of-light measuring sensitivity $S_{c\lambda}$ reaches a maximum are calculated from Eq. (17).

In the case that the measurement is performed after the sample to be measured is put into the cell at the measurement stage, quantities of transmitted light corresponding to the portions of the optimum optical path lengths $L_{pj}$ are measured and stored.

Then, by the arithmetic unit 4, $A_{cj}$ is calculated from Eq. (3) based on the resulting quantities of transmitted light $I_{ij}$ (j=1 to m), and further the concentration of the k component (k=1 to n) is calculated by multivariate analysis. Thus, calculation results are outputted.

The above calculation process can be summarized into the steps of:

1) Previously determining the constant $\delta$ (=$\exp\alpha_c l$),

1') Measuring the quantity of transmitted light passed through the cell having no liquid sample, and calculating the quantity of light $I_o$ using Eq. (2), 2) Previously determining $\gamma_o$ from Eq. (2) by measuring the quantity of transmitted light $I_{ot}$ at the reference optical path length $L_o$ by using a sample of the reference concentration, 3) Calculating the value of $k_p$ from Eq. (18), 4) Calculating $L_{p\lambda}$ from Eq. (17) (L corresponding to $k_p$ is $L_{p\lambda}$), 5) Repeating the calculations of steps 3) and 4) for a plurality of wavelengths of light, 6) Calculating the absorbance $A_{c\lambda}$ at $L_{p\lambda}$ for each wavelength from Eq. (4), in the case that measurement is performed on a sample whose concentration is unknown and 7) Calculating the concentration of i component in the sample by multivariate analysis.

Next described is the method for optically measuring concentrations of components according to the twelfth aspect of the present invention which is applied, for example, to the apparatus as shown in FIG. 1.

At step 1, in a state that the cell 1 does not contain sample 11, the quantity of transmitted light of a wavelength $\lambda$ that has been emitted from the variable-wavelength laser generator 12 and transmitted through the cell 1 is measured by the photodetector 3 and the quantity of incident light $I_o$ is calculated by the arithmetic unit 4 from Eq. (2).

At step 2, in reference concentration sample, the transmissivity $t_s$ that depends on the refractive index of the light of wavelength $\lambda$ is calculated by the arithmetic unit 4.

At step 3, in a state that the cell 1 contains reference concentration sample, and the optical path length L is set to $L_o$, the quantity of transmitted light $I_{to}$ of wavelength $\lambda$ is measured by the photodetector 3.

At step 4, for the reference optical path length $L_o$ and the light of wavelength $\lambda$, the value $\gamma_o$ of $\gamma$ is calculated by the arithmetic unit 4 from Eq. (2).

At step 5, the optical path length ratio $k_p$ corresponding to an optical path length $L_p$ at which the quantity-of-light measuring sensitivity S defined by Eq. (5) reaches a maximum for the wavelength $\lambda$ is calculated by the arithmetic unit 4 from Eq. (18).

At step 6, the optimum optical path length $L_{p\lambda a}$ at which the quantity-of-light measuring sensitivity S reaches a maximum for the wavelength $\lambda$ is calculated by the arithmetic unit 4 from Eq. (17).

Then, the above steps 1 through 6 are repeated a plurality of times for different wavelengths $\lambda$. Based on the calculated optimum optical path length $L_{p\lambda}$ for each wavelength $\lambda$, concentrations of components in the sample are calculated by the arithmetic unit 4 by multivariate analysis, and calculation results are output.

Next described is the method for optically measuring concentrations of components according to the thirteenth aspect of the present invention which is applied, for example, to the apparatus as shown in FIG. 1.

At step 1, in a state that the cell 1 does not contain sample, the quantity of transmitted light of a wavelength $\lambda$ that has been emitted from the variable-wavelength laser generator 12 and transmitted through the cell 1 is measured by the photodetector 3 and the quantity of incident light $I_o$ is calculated by the arithmetic unit 4 from Eq. (2).

At step 2, in reference concentration sample, the transmissivity $t_s$ that depends on the refractive index of the light of a wavelength $\lambda$ is calculated by the arithmetic unit 4.

At step 3, in a state that the cell 1 contains the reference concentration sample, and the optical path length is set to L, the quantity of transmitted light $I_{tL}$ of the light of the wavelength $\lambda$ is measured by the photodetector 3.

At step 4, the absorbances $A_{c\lambda}$ for the light of the wavelength $\lambda$ at portions of the cell corresponding to different optical path lengths L are calculated by the arithmetic unit 4 from the following equation:

$$\log_e(I_o/I_t) - \log_e(1/t) - \alpha_c l = A_c$$

where $$A_c = \Sigma \alpha_i C_i L$$

At step 5, the absorbance $A_{c\lambda p}$ equal to $\log_e e$ from among the absorbances $A_{c\lambda}$ for the light of the wavelength λ is determined by the arithmetic unit 4.

At step 6, the optical path length $L_p$ corresponding to the absorbance $A_{c\lambda p}$ for the light of the wavelength λ is stored by the arithmetic unit 4.

Then, based on values of quantity of transmitted light at positions of the optimum optical path lengths $L_{p\lambda}$ for different wavelengths λ calculated by repeating the above steps 1 through 6 a plurality of times for different wavelengths λ, concentrations of components in the sample are calculated by the arithmetic unit 4 by multivariate analysis, and calculation results are outputted.

As described above, according to the measuring methods, the concentration of the i component in the sample 11 is calculated and outputted by the arithmetic unit 4 from measurement data of large S/N ratios at optimum optical path lengths $L_{p\lambda}$. Accordingly, the accuracy of concentration measurement is enhanced so that, for example when the concentrations of the i component have small differences among different samples, the apparatus can measure the concentration of the i component with high accuracy.

Also, the above-described measuring methods are applicable also to the apparatuses according to the second to eleventh aspects of the present invention.

Further, it is preferable that the light used in the above embodiments has a wavelength of the near-infrared region.

As apparent from the above description, according to the present invention, the apparatus for optically measuring concentrations of components comprises: a cell for containing a sample therein, the cell being capable of changing its internal optical path length; a light irradiator for irradiating light of a selected wavelength to the cell, the light irradiator being capable of changing the wavelength of light to be irradiated; a photodetector for receiving light that has been transmitted through the cell to detect quantity of the transmitted light; and an arithmetic unit for calculating and storing for each wavelength an optical path length at which a peak value of quantity-of-light measuring sensitivity with respect to the quantity of transmitted light detected by the photodetector takes place, and calculating concentration of a component contained in the sample based on values of the quantity of transmitted light and values of the optical path length at peak positions, the values having been stored for each wavelength, and for outputting calculation results.

Thus, it becomes possible to determine concentrations of components from intensities of transmitted light at optimum optical path lengths at which the S/N ratio reaches a maximum. Therefore, the measurement accuracy of concentrations can be enhanced regardless of whether the differences in concentration of one component among samples are large or small.

Also, according to another aspect of the present invention, the method for optically measuring concentrations of components comprises: a step for irradiating light of a wavelength selected by a light emitter capable of generating light of different wavelengths, to a cell containing a sample and which is capable of changing optical path length over which light is transmitted; a step for detecting quantity of transmitted light for each optical path length when the photodetector has received light transmitted through the cell, the above steps being repeatedly performed for a plurality of wavelengths; and a step for calculating and storing for each wavelength an optical path length at which a peak value of quantity-of-light measuring sensitivity with respect to the quantity of transmitted light detected by the photodetector takes place, and calculating concentration of a component contained in the sample based on values of the quantity of transmitted light and values of the optical path length at peak positions, and for outputting calculation results, the step being performed by an arithmetic unit.

Further, according to yet another aspect of the present invention, the method for optically measuring concentrations of components comprises:

(i) a step for measuring quantity of transmitted light of a wavelength λ that has been emitted from a light source and transmitted through a cell which does not contain the sample, and calculating a quantity of incident light $I_o$ by the following equation:

$$I_i = I_o t \gamma$$

(ii) a step for calculating a transmissivity $t_s$ in a reference concentration sample, that depends on the refractive index of the light of wavelength λ, (iii) a step for measuring a quantity of transmitted light $I_{to}$ of the light of wavelength λ when an optical path length L within the cell is set to a reference optical path length $L_o$, in a state that the cell contains the reference concentration sample, (iv) a step for calculating a value $\gamma_o$ of γ for light with the reference optical path length $L_o$ and the wavelength λ by the following equation:

$$I_t = I_o t \gamma$$

(v) a step for calculating an optical path length ratio $k_p$ corresponding to an optical path length $L_p$ at o which quantity-of-light measuring sensitivity S becomes a maximum with the wavelength λ, by the following equation:

$$k = -1/\log_e(\gamma_o \delta)$$

the quantity-of-light measuring sensitivity S being defined by the following equation:

$$S = dI_t/dC_i$$

(vi) a step for calculating an optimum optical path length $L_{p\lambda}$ at which the quantity-of-light measuring sensitivity S reaches a maximum with the wavelength λ, by the following equation:

$$k = L/L_o$$

the above steps being performed repeatedly a plurality of times with the wavelength λ varied, to calculate values of quantity of transmitted light at positions of optimum optical path lengths $L_{p\lambda}$ corresponding to the varied wavelengths λ, wherein concentration of a component contained in the sample is calculated by multivariate analysis based on the calculated values of quantity of transmitted light.

Furthermore, according to still another aspect of the present invention, the method for optically measuring concentrations of components comprises:

(i) a step for measuring quantity of transmitted light of a wavelength λ that has been emitted from a light source and transmitted through the cell, in a state that the cell does not contain the sample, and calculating a quantity of incident light $I_o$ by the following equation:

$$I_t = I_o t\gamma$$

(ii) a step for calculating a transmissivity $t_s$, in a reference concentration sample, that depends on the refractive index of the light of wavelength $\lambda$, (iii) a step for measuring a quantity of transmitted light $I_{tL}$ Of the light of wavelength $\lambda$ with an optical path length L within the cell containing the reference concentration sample, (iv) a step for calculating absorbances $A_{c\lambda}$ to the light of wavelength $\lambda$ at portions of the cell corresponding to different optical path lengths L, by the following equation:

$$\log_e(I_o/I_t) - \log_e(1/t) - \alpha_c l = A_c$$

(v) a step for determining an absorbance $A_{c\lambda_p}$ equal to $\log_e e$ from among the absorbances $A_{c\lambda}$ to the light of wavelength $\lambda$, and (vi) a step for storing an optical path length $L_p$ corresponding to the absorbance $A_{c\lambda_p}$ to the light of wavelength $\lambda$, the above steps being performed repeatedly a plurality of times with the wavelength $\lambda$ varied, to calculate values of quantity of transmitted light at positions of optimum optical path lengths $L_{p,\lambda}$ corresponding to the varied wavelengths $\lambda$, wherein concentration of a component contained in the sample is calculated by multivariate analysis based on the calculated values of quantity of transmitted light.

Thus, the measurement accuracy of concentrations can be enhanced regardless of whether the differences in concentration of one component among samples are large or small, as in the foregoing case, advantageously.

What is claimed is:

1. An apparatus for optically measuring concentrations of components, comprising:

a cell for containing a sample therein;

means for presenting different optical path lengths to light transmitted through said cell;

a light irradiator for emitting light of a selected wavelength to the cell;

means for changing the wavelength of light emitted by said light irradiator;

a photodetector for receiving light that has been transmitted through the cell to detect a quantity of transmitted light; and an arithmetic unit for calculating and storing, for each wavelength, an optimum optical path length of said different optical path lengths at which a peak value of quantity-of-light measuring sensitivity with respect to the quantity of transmitted light detected by the photodetector occur, for calculating a concentration of a component contained in the sample based on values of the quantity of transmitted light at the optimum optical path length, the values having been stored for each wavelength emitted by said light irradiator, and for outputting calculation results.

2. The apparatus for optically measuring concentrations of components according to claim 1, wherein said cell simultaneously presents continuously or stepwise different optical path lengths.

3. The apparatus for optically measuring concentrations of components according to claim 2, wherein different portions on said photodetector correspond to different optical path lengths simultaneously presented by said cell.

4. The apparatus for optically measuring concentrations of components according to claim 3, wherein a slope of an input face of said photodetector is parallel to a slope of an output face of said cell, such that a distance traversed by the transmitted light from said cell to said photodetector remains constant for light being transmitted through different optical path lengths internally in said cell.

5. The apparatus for optically measuring concentrations if components according to claim 1, wherein said cell has variable optical path length.

6. The apparatus for optically measuring concentrations of components according to any one of claims 1, 2 or 5, wherein said light irradiator is a laser.

7. The apparatus for optically measuring concentrations of components according to claim 6, wherein said laser is a variable-wavelength laser.

8. The apparatus for optically measuring concentrations of components according to any of claims 1, 2 or 5, wherein said light irradiator comprises a variable-wavelength laser, and a measuring system for enlarging and collimating a laser beam output from the variable-wavelength laser.

9. The apparatus for optically measuring concentrations of components according to any one of claims 1, 2 or 5, wherein said light irradiator comprises a rotatable mirror for, upon reception of a laser beam, changing a direction in which the laser beam is reflected, and a measuring system for directing the reflected laser beam toward a specified direction.

10. The apparatus for optically measuring concentrations of components according to any one of claims 1, 2 or 5 wherein said light irradiator comprises a light emitter for emitting light including different wavelengths, and a measuring system for collimating the emitted light and including a filter means for allowing light only of a selected wavelength out of the light including different wavelengths to be incident upon the cell.

11. The apparatus for optically measuring concentrations of components according to any one of claims 1, 2 or 5, further comprising a quantity-of-light detection means for detecting quantity of light when said photodetector has received selected light.

12. The apparatus for optically measuring concentrations of components according to any one of claims 1, 2 or 5, wherein said photodetector comprises a spectrometer.

13. A method for optically measuring concentrations of components, comprising the steps of:

selecting a wavelength to be emitted;

emitting light of the wavelength selected to a cell which contains a sample;

presenting different optical path length over which light is transmitted through said cell;

detecting a quantity of transmitted light for each of said different optical path lengths when a photodetector has received light transmitted through the cell;

repeating the above steps for a plurality of wavelengths;

calculating and storing for each wavelength of said plurality of wavelengths an optimum optical path length at which a peak value of quantity-of-light measuring sensitivity with respect to the quantity of transmitted light detected by the photodetector takes place; and calculating concentration of a component contained in the sample based on values of the quantity of transmitted light at the optimum optical path length at peak positions for each of said plurality of wavelengths, and outputting calculation results.

14. A method for optically measuring concentrations of components, comprising the steps of:

(i) measuring quantity of transmitted light of a wavelength $\lambda$ that has been emitted from a light source and transmitted through a cell which does not contain a sample, and calculating a quantity of incident light $I_o$ by the following equation:

$$I_t = I_o t \gamma$$

wherein $I_o$=quantity of light incident upon the cell,
$I_t$=quantity of light transmitted through the cell,
$\gamma = \exp(-\Sigma \alpha_i C_i L - \alpha_c l)$
$l = l_1 + l_2$
$t : t_1 t_2 t_3 t_4 = (n_o, n_c n)$
$t_i$=transmissivity at i interface,
$\alpha_i$=extinction coefficient of i component (a function of wavelength),
$\alpha_c$=extinction coefficient of the cell (a function of wavelength),
$l_1, l_2$=wall thicknesses on both sides of the cell, and
$n, n_o, n_c$=refractive indexes of sample, air, and cell, respectively;

(ii) calculating a transmissivity $t_s$ that depends on a refractive index of the light of wavelength $\lambda$ in a reference concentration sample;

(iii) measuring a quantity of transmitted light $I_{to}$ of the light of wavelength $\lambda$ when an optical path length L within the cell is set to a reference optical path length $L_0$, in a state that the cell contains the reference concentration sample;

(iv) calculating a value $\gamma_o$ of $\gamma$ or light with the reference optical path length $L_o$ and the wavelength $\lambda$ by the following equation:

$$I_t = I_o t \gamma$$

(v) calculating an optical path length ratio $k_p$ corresponding to an optical path length $L_p$ at which quantity-of-light measuring sensitivity S reaches a maximum with the wavelength $\lambda$, by the following equation:

$$k = -1/\log_e(\gamma_o^\delta)$$

where $$\delta = \exp(\alpha_c l)$$

the quantity-of-light measuring sensitivity S being defined by the following equation:

$$S = d I_t / dC_i$$

where

S=quantity-of-light measuring sensitivity,
$dI_t$=variation of quantity of transmitted light $I_t$ based on variation $dC_i$ of i component concentration, and
$dC_i$=variation of i component concentration, (vi) calculating an optimum optical path length $L_{p\lambda}$ at which the quantity-of-light measuring sensitivity S reaches a maximum with the wavelength $\lambda$, by the following equation:

$$k = L/L_o$$

repeating the above steps a plurality of times with the wavelength $\lambda$ varied, to calculate values of quantity of transmitted light at positions of optimum optical path lengths $L_{p\lambda}$ corresponding to the varied wavelengths $\lambda$, wherein concentration of a component contained in the sample is calculated by multivariate analysis based on the calculated values of quantity of transmitted light.

15. A method for optically measuring concentrations of components, comprising the steps of:

(i) measuring quantity of transmitted light of a wavelength $\lambda$ that has been emitted from a light source and transmitted through a cell wherein a sample is not contained and calculating a quantity of incident light $I_o$ by the following equation:

$$I_t = I_o t \gamma$$

wherein $I_o$=quantity of light incident upon the cell,
$I_t$=quantity of light transmitted through the cell,
$\gamma = \exp(-\Sigma \alpha_i C_i L - \alpha_c l)$
$l = l_1 + l_2$
$t : t_1 t_2 t_3 t_4 = (n_o, n_c n)$
$t_i$=transmissivity at i interface,
$\alpha_i$=extinction coefficient of i component (a function of wavelength),
$\alpha_c$=extinction coefficient of the cell (a function of wavelength),
$C_i$=concentration of i component in the sample,
$l_1, l_2$=wall thicknesses on both sides of the cell, and
$n, n_o, n_c$=refractive indexes of sample, air, and cell, respectively, (ii) calculating a transmissivity $t_s$ that depends on a refractive index of the light of wavelength $\lambda$ in a reference concentration sample, (iii) measuring a quantity of transmitted light $I_{tL}$ of the light of wavelength $\lambda$ when an optical path length L within the cell containing the reference concentration sample, (iv) calculating absorbances to the light of wavelength $\lambda$ at portions of the cell corresponding to different optical path lengths L, by the following equation:

$$\log_e(I_o/I_t) - \log_e(1/t) - \alpha_c l = A_c$$

where $$A_c = \Sigma \alpha_i C_i L$$

(v) determining an absorbance $A_{c\lambda p}$ equal to $\log_e e$ from among the absorbances $A_{c\lambda}$ to the light of wavelength $\lambda$, and (vi) storing an optical path length $L_p$ corresponding to the absorbance $A_{c\lambda p}$ to the light of wavelength $\lambda$ repeating the above steps a plurality of times with the wavelength $\lambda$ varied, to calculate values of quantity of transmitted light at positions of optimum optical path lengths $L_{p\lambda}$ corresponding to the varied wavelengths $\lambda$, wherein concentration of a component contained in the sample is calculated by multivariate analysis based on the calculated values of quantity of transmitted light.

16. An apparatus for optically measuring concentrations of components comprising:

a light irradiator for emitting light of a selected wavelength towards a cell containing a sample therein, where the light is collimated into a plurality of light beams by a light collimating means, before entering said cell;

wherein said cell presents simultaneous multiple optical path lengths where each one of the collimated light beams simultaneously traverses a different one of the simultaneous multiple optical path lengths;

means for changing the wavelength of light emitted by said light irradiator;

a photodetector for receiving said light beams which have transmitted through said cell to detect a quantity of the transmitted light beams;

an arithmetic unit for calculating and storing, for each wavelength of the emitted light, an optimum optical path length, based on said simultaneous multiple optical path lengths, at which a peak value of quantity-of-light sensitivity with respect to the quantity of transmitted light beams at the optimum optical path length, the values having been stored for each wavelength omitted by said light irradiator, and for outputting calculation results.

* * * * *